(12) United States Patent
Brazil et al.

(10) Patent No.: US 12,109,125 B2
(45) Date of Patent: Oct. 8, 2024

(54) INTERVERTEBRAL FUSION CAGE IMPLANT AND SURGICAL PROCEDURE THEREFOR

(71) Applicant: SIGNATURE ORTHOPAEDICS EUROPE LTD, Dublin (IE)

(72) Inventors: Declan Brazil, Lane Cove West (AU); Andrew Roginsky, Mullingar (IE); David Edis, Mount Martha (AU)

(73) Assignee: SIGNATURE ORTHOPAEDICS EUROPE LTD, Dublin (IE)

( * ) Notice: Subject to any disclaimer, the term of this patent is extended or adjusted under 35 U.S.C. 154(b) by 522 days.

(21) Appl. No.: 17/594,857

(22) PCT Filed: Aug. 24, 2021

(86) PCT No.: PCT/AU2021/050939
§ 371 (c)(1),
(2) Date: Nov. 1, 2021

(87) PCT Pub. No.: WO2022/040731
PCT Pub. Date: Mar. 3, 2022

(65) Prior Publication Data
US 2022/0304819 A1    Sep. 29, 2022

(30) Foreign Application Priority Data
Aug. 26, 2020 (AU) .............................. 2020903045

(51) Int. Cl.
*A61F 2/44* (2006.01)
*A61F 2/30* (2006.01)

(52) U.S. Cl.
CPC .... *A61F 2/447* (2013.01); *A61F 2002/30322* (2013.01); *A61F 2002/30593* (2013.01);
(Continued)

(58) Field of Classification Search
CPC ............ A61F 2/447; A61F 2002/30322; A61F 2002/30593; A61F 2002/30785; A61F 2002/30828; A61F 2002/30904
See application file for complete search history.

(56) References Cited

U.S. PATENT DOCUMENTS

| | | | |
|---|---|---|---|
| 9,125,754 B2 * | 9/2015 | Duggal | ................. A61F 2/4657 |
| 2003/0004576 A1 * | 1/2003 | Thalgott | ............... A61F 2/4611 623/17.16 |

(Continued)

OTHER PUBLICATIONS

International Search Report & Written Opinion dated Oct. 6, 2021 from PCT Application No. PCT/AU2021/050939.

*Primary Examiner* — Nicholas J Plionis
(74) *Attorney, Agent, or Firm* — INNOVATION CAPITAL LAW GROUP, LLP; Vic Lin

(57) ABSTRACT

An intervertebral fusion cage implant is generally elongate and defines superior and inferior bearing surfaces. The inferior bearing surface has vertebral body engaging interferences and the superior bearing surface has a substantially smooth surface profile, sagittal plane convexity and sagittal plane curvature asymmetry. The sagittal plane convexity defines a saggital plane axis rising anteriorly with respect to a horizontal saggital plane axis. The superior bearing surface defines a central section having coronal plane convexity and lateral sections adjacent the central section.

20 Claims, 4 Drawing Sheets

(52) U.S. Cl.
CPC ............... *A61F 2002/30785* (2013.01); *A61F 2002/30828* (2013.01); *A61F 2002/30904* (2013.01)

(56) References Cited

U.S. PATENT DOCUMENTS

| | | |
|---|---|---|
| 2003/0023306 A1 | 1/2003 | Liu et al. |
| 2007/0250167 A1 | 10/2007 | Bray et al. |
| 2007/0255416 A1 | 11/2007 | Melkent et al. |
| 2009/0187246 A1 | 7/2009 | Foley |
| 2013/0023990 A1 | 1/2013 | Zipnick et al. |
| 2015/0032210 A1 | 1/2015 | Stinchfield et al. |
| 2016/0310294 A1 | 10/2016 | McConnell et al. |
| 2020/0188130 A1 | 6/2020 | Jebsen et al. |

\* cited by examiner

INTERVERTEBRAL FUSION CAGE IMPLANT AND SURGICAL PROCEDURE THEREFOR

FIELD OF THE INVENTION

This invention relates generally to an intervertebral fusion cage implant and surgical procedure therefor.

BACKGROUND OF THE INVENTION

Surgical intervention for the treatment of misaligned spinal columns may involve insertion of an intervertebral fusion cage implant by open incision or laparoscopic procedure to fuse two or more vertebrae in the lumbar spine together.

An intervertebral fusion cage implant is a type of cylinder which is inserted between vertebrae endplates after removing the intervertebral disc, which spreads the two vertebrae apart and acts as a cage implant for bone graft to allow intervertebral fusion to occur between the two vertebrae.

The endplate is the interface between the vertebral trabeculae and intervertebral disc and comprises the cartilaginous endplate and osseous endplate. The osseous endplate forms a shell of the vertebral body and thus known as the vertebral endplate.

A vertebral endplate consists of the epiphyseal rim, which is a ring of smooth relatively solid and strong bone at the peripheral margin of the endplate and the central endplate which is relatively thin in comparison.

However, improper contact between the bearing surfaces of the fusion cage implant and the vertebral endplates can cause malunion or subsidence, and the present invention seeks to provide an intervertebral fusion cage implant which will overcome or substantially ameliorate at least some of the deficiencies of the prior art, or to at least provide an alternative.

It is to be understood that, if any prior art information is referred to herein, such reference does not constitute an admission that the information forms part of the common general knowledge in the art, in Australia or any other country.

SUMMARY OF THE DISCLOSURE

The present intervertebral fusion cage implant is generally elongate and has opposite superior and inferior bearing surfaces. The inferior bearing surface has vertebral body engaging interferences to engage a lower vertebra and the superior bearing surface has a substantially smooth surface profile and sagittal plane convexity to allow an upper vertebra to be moved along and in contact with the smooth superior bearing surface as corrective forces are applied to manipulate the upper vertebra into alignment.

As such, when placing the implant, the inferior bearing surface engages the endplate of the lower vertebral body whilst the surgeon slides the upper vertebral body over the superior bearing surface in the sagittal plane to correct lordosis, Once in the correct position, the upper vertebral body may be fixed with pedicle screws.

The present intervertebral fusion cage can be placed with Oblique Lumbar Interbody Fusion (OLIF) or Direct Lumbar Interbody Fusion (DLIF) techniques.

The superior bearing surface defines a central section having coronal plane convexity and lateral sections adjacent the central section. The implant is sized so that the central section bears against a central endplate of the upper vertebra in use and the lateral sections bear against opposite sides of the epiphyseal rim of upper vertebra.

The shape of the central section and the lateral sections increase contact surface area with the endplate, reducing likelihood of gaps between the implant and the endplate which could prevent graft material coming into contact with the bone.

Furthermore, the lateral sections bear between the relatively harder epiphyseal rim to support the loading of the central section against the relatively thin and porous central endplate, thereby preventing or reducing the likelihood of the implant subsiding which can cause malunion, and restoration loss.

The superior bearing surface also has sagittal plane curvature asymmetry (i.e. the sagittal plane curvature is not symmetric in the sagittal plane about a longitudinal axis) derived from cadaver studies to better fit empirical endplate concavity which may differ superiorly and inferiorly.

Furthermore, the sagittal plane convexity is angled (i.e. defining a sagittal plane axis anteriorly rising with respect to a horizontal sagittal plane axis) to maintain contact with the central section and the lateral wings even once lordotic correction is achieved.

As such, the present implant morphometrics can maximise graft material volume and contact, protect the disc space from subsidence, anatomically conform to empirical endplate concavity and maintain contact even once lordotic correction is achieved.

Other aspects of the invention are also disclosed.

BRIEF DESCRIPTION OF THE DRAWINGS

Notwithstanding any other forms which may fall within the scope of the present invention, preferred embodiments of the disclosure will now be described, by way of example only, with reference to the accompanying drawings in which.

DESCRIPTION OF EMBODIMENTS

Figure 1:
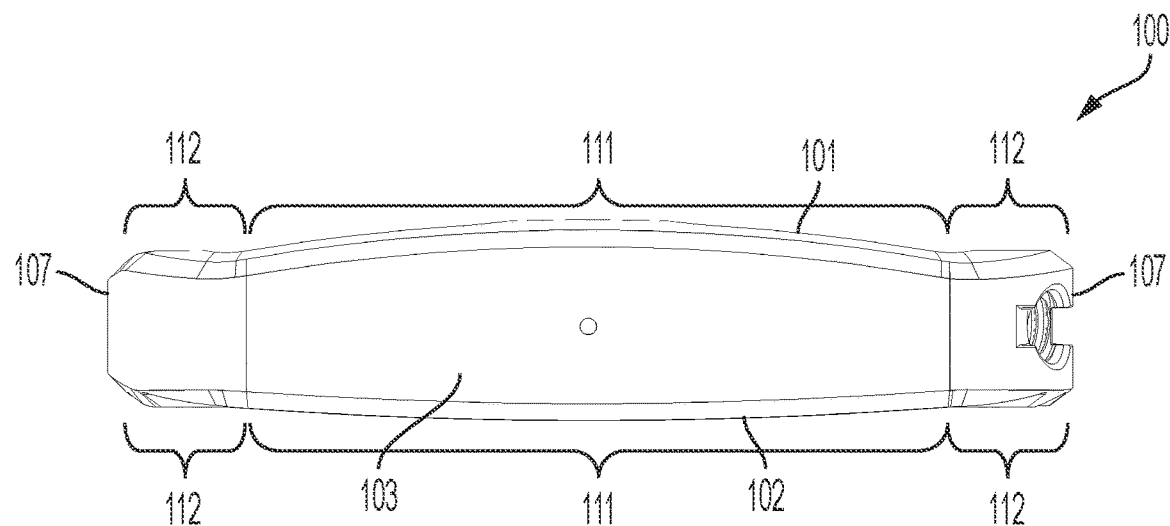
FIG. 1 shows an anterior elevation view of an intervertebral fusion cage implant in accordance with an embodiment.
Figure 2:
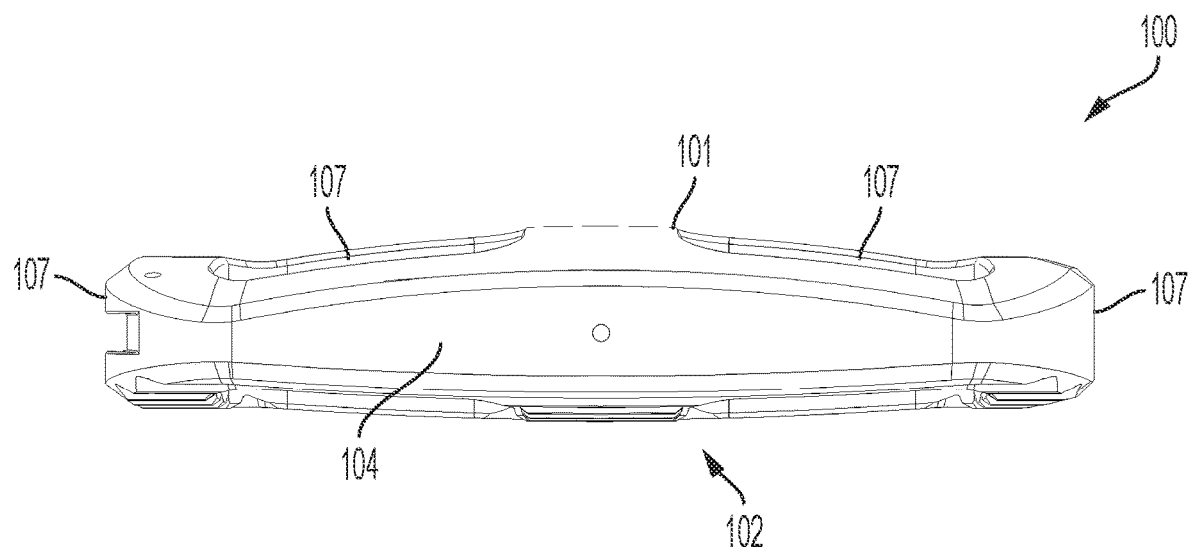
FIG. 2 shows a posterior elevation view of the implant.
Figure 3:
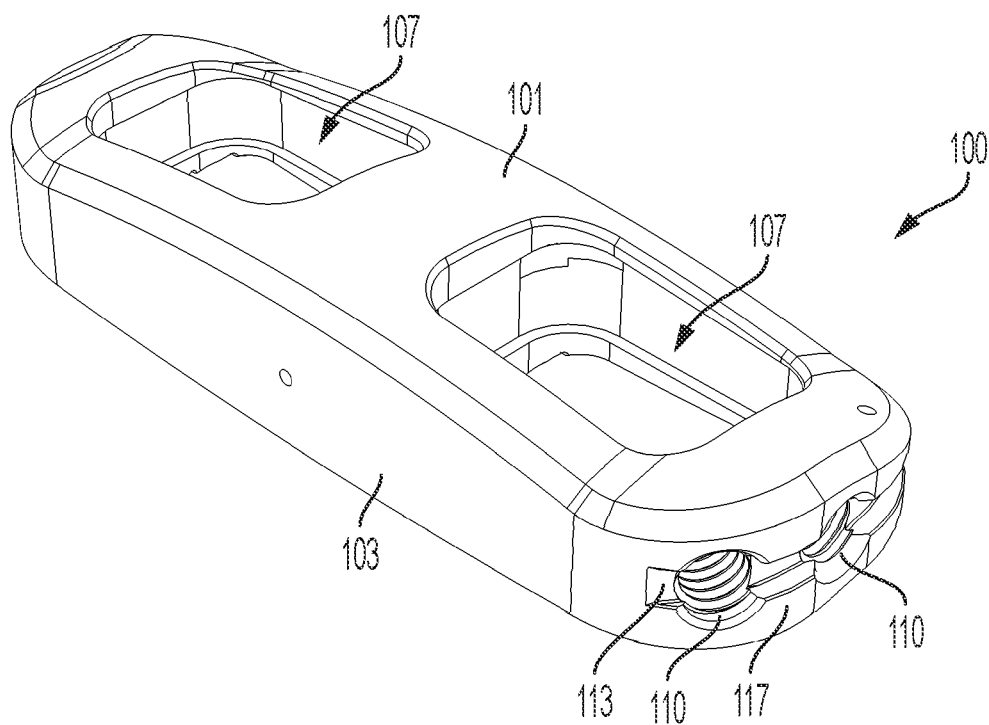
FIG. 3 shows a superior perspective view of the implant.
Figure 4:
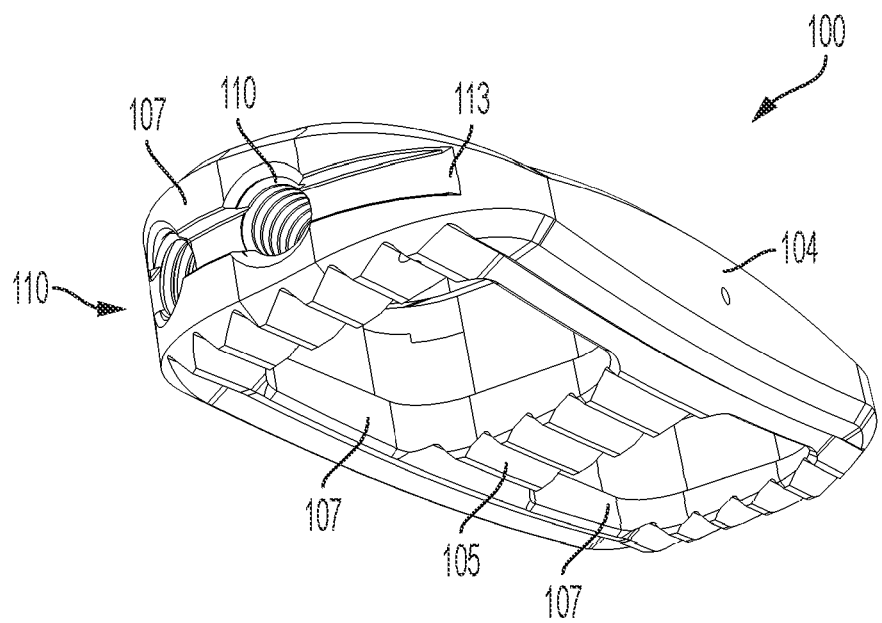
FIG. 4 shows an inferior perspective view of the implant.
Figure 5:
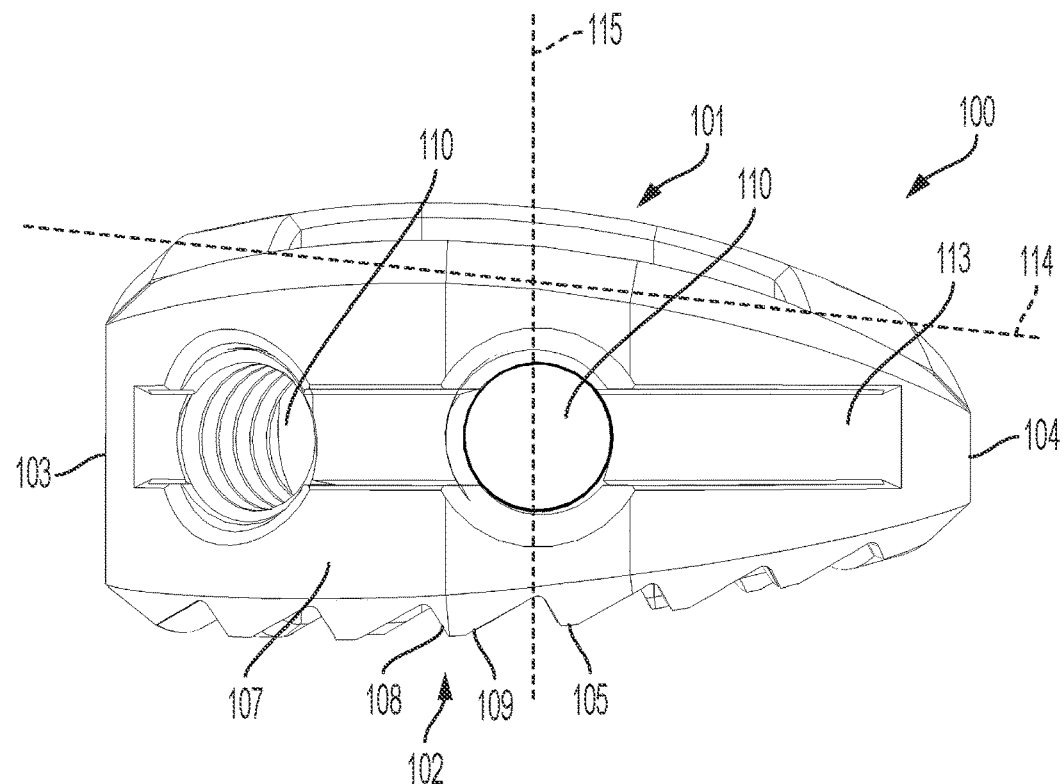
FIG. 5 shows a lateral elevation view of the implant according to a first size.
Figure 6:
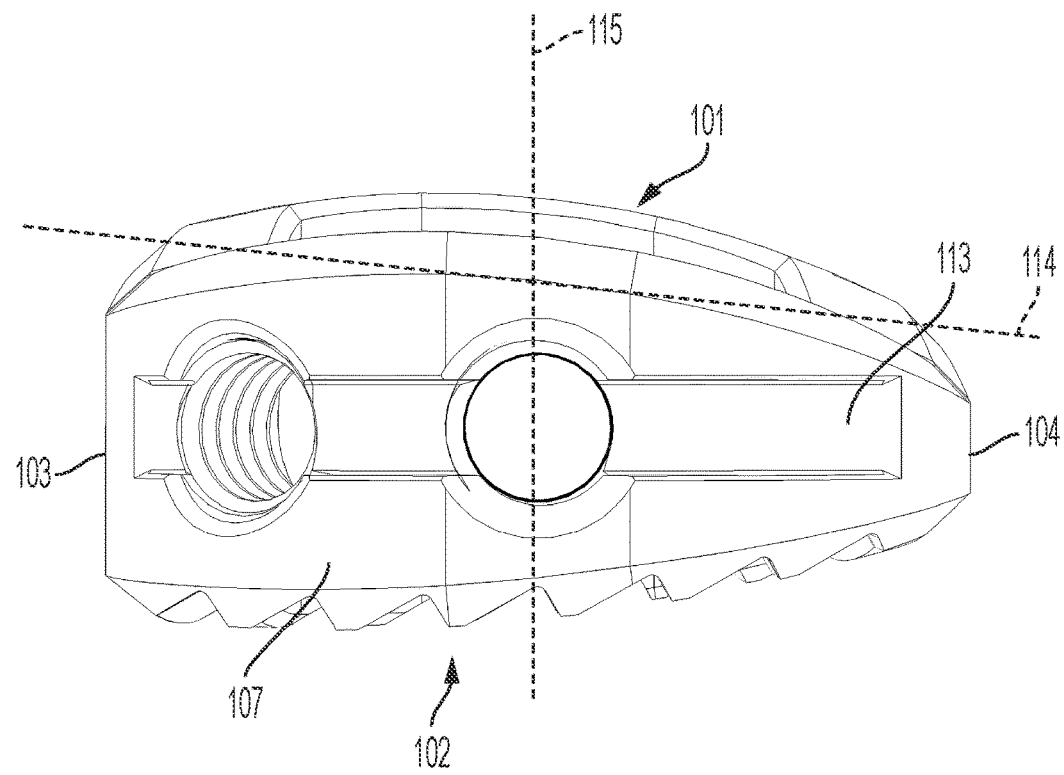
FIG. 6 shows a lateral elevation view of the implant according to a second size.
Figure 7:
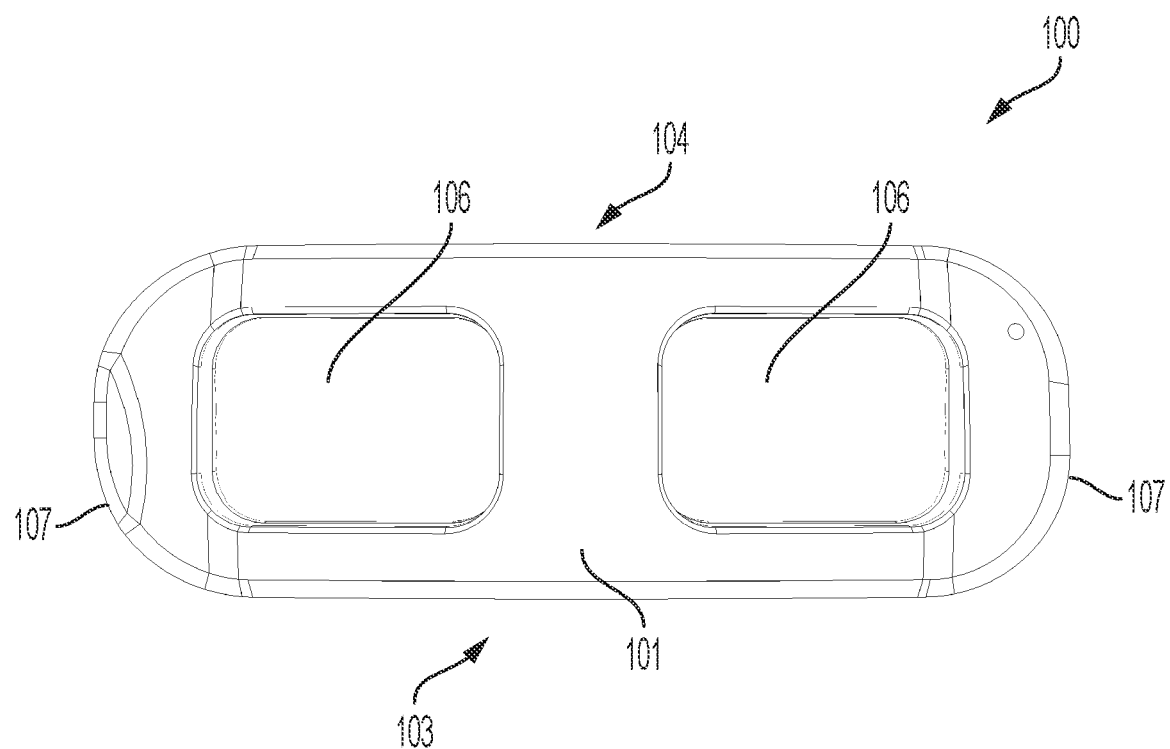
FIG. 7 shows a superior plan view of the implant.

An intervertebral fusion cage implant 100 will be described hereunder with reference to the anatomical planes and axes wherein FIG. 1 shows an anterior elevation view of the cage implant and FIG. 2 shows a posterior elevation view of the implant 100. FIG. 3 shows a superior perspective view of the implant 100 and FIG. 4 shows an inferior perspective view of the implant 100. FIGS. 5 and 6 show lateral elevation views of the implant 100 of two different sizes. FIG. 7 shows a superior plan view of the implant 100.

As such, lateral and derivatives thereof generally mean at or towards the sides and medial generally means at or towards the middle therebetween. Similarly, anterior means at or towards the front and posterior means towards at or towards the rear. A superior/inferior axis generally extends from top to bottom, a lateral or mediolateral axis generally extends from side to side and an anteroposterior axis generally extends front to back.

The sagittal plane lies on the superior/inferior and anteroposterior axes, the coronal plane lies on the superior/inferior and mediolateral axes and the transverse plane lies on the mediolateral and anteroposterior axes.

The implant 100 is generally elongate and defines a superior bearing surface 101 and an inferior bearing surface 102.

With reference to FIG. 4, the inferior bearing surface 102 has vertebral body engaging interferences 105.

The superior bearing surface 101 has a substantially smooth surface profile. With reference to FIGS. 5 and 6, the superior bearing surface 101 has sagittal plane convexity.

The sagittal plane convexity is angled posteriorly. In other words, with reference to FIGS. 5 and 6, the sagittal plane convexity defines a saggital plane axis 114 anteriorly rising with respect to the horizontal saggital plane axis.

The sagittal plane curvature is further asymmetric. In other words, again with reference to FIGS. 5 and 6, the sagittal plane curvature is not symmetric in the sagittal plane about a longitudinal axis 115.

With reference to FIG. 1, the superior bearing surface 101 defines a central section 111 having coronal plane convexity and lateral sections 112 adjacent the central section 111. The central section 111 extends superiorly with respect to the lateral sections 112.

The implant 100 is sized so that the central section 111 bears against a central endplate of an adjacent vertebra in use and the lateral sections 112 bear against opposite sides of an epiphyseal rim of the adjacent vertebra in use.

The implant 100 may further define an anterior surface 103, a posterior surface 104 and lateral surfaces 107. With reference to FIG. 7, the anterior and posterior surfaces 103, 104 may be generally planar. With reference to FIGS. 1 and 2, the lateral surfaces 107 may be planar in the coronal plane.

The inferior bearing surface 102 may also have sagittal plane convexity. Furthermore, superior bearing surface 101 and the inferior bearing surface 102 may be nonsymmetric in the coronal plane. As shown in FIG. 1, the superior bearing surface 101 may exhibit greater curvature than that of the inferior bearing surface 102 in the coronal plane.

Similarly, the superior bearing surface 101 and the inferior bearing surface 102 may be nonsymmetric in the sagittal plane as is evident from FIGS. 5 and 6 wherein the superior bearing surface 101 may exhibit greater curvature as compared to the inferior bearing surface 102 in the sagittal plane.

With further reference to FIGS. 5 and 6, the implant 100 may be wider in the sagittal plane towards the anterior surface 103 as compared to towards the posterior surface 104.

With reference to FIG. 1, a central section of 111 the inferior bearing surface 102 may also exhibit coronal plane convexity.

In use, the implant 100 is inserted between respective endplates of two vertebral bodies, referred to herein as upper and lower vertebral bodies with respect to the implant 100.

The superior bearing surface 101 is anteroposteriorly smooth to allow movement of the upper vertebral body over the superior bearing surface 101 in the sagittal plane.

In this regard, the superior bearing surface 101 may be generally smooth anteroposteriorly to allow the upper vertebral body to slide over the superior bearing surface 101 in the sagittal plane. However, in embodiments shown, the superior bearing surface 101 is also smooth mediolaterally so that the upper vertebral body may also slide over the superior bearing surface 101 in the coronal plane.

The interferences 105 may be anteroposteriorly operative to resist anterior movement of the inferior vertebral body in the sagittal plane. In embodiments shown, the interferences comprise serrations 105 which may run mediolaterally.

With reference to FIG. 5, each serration 105 may be orientated anteriorly wherein an anterior edge 108 thereof is at a greater angle with respect to the transverse plane with respect to a posterior edge 109 thereof to resist lordotic expulsion.

The implant 100 may comprise at least one osseointegration cavity 106 open between the superior bearing surface 101 and the inferior bearing surface 102. As is best shown in FIG. 7, the implant 100 may comprise a pair of osseointegration cavities 106. The osseointegration cavities 106 may be spaced laterally such that both the superior and inferior bearing surfaces 101, 102 are continuous therebetween in the sagittal plane.

The osseointegration cavities 106 may be generally rectangular as is also best shown in FIG. 7.

At least one lateral face 107 may define at least one threaded placement instrument socket 110 therein which engage a placement instrument for placing the implant 100 during surgery. In the embodiment shown, the implant 100 comprises first and second placement instrument sockets 110, a first of which is orientated generally laterally wherein a second of which is orientated more anteriorly. The anterolateral socket 110 allows for the implant 100 to be placed or removed at the angle with a placement instrument.

One of the lateral faces 107 may comprise a longitudinal slot 113 for engaging a placement instrument to dissipate loads experience during placement throughout the connection between the implant 100 and the instrument.

With reference to FIG. 1, the lateral sections 112 may extend parallel with respect to the horizontal plane or rise laterally with respective horizontal plane. In other words, the lateral sections 112 define a horizontal or laterally upwardly rising edge which more firmly engages the harder epiphyseal rim of the vertebral body endplate and resists longitudinal axis forces to support the central section 112 which conformingly engages the cancellous central concave endplate region of the adjacent vertebral body.

In embodiments, the inferior bearing surface 102 may similarly comprise the central section 111 and the lateral sections 112. As is best shown in FIG. 1, vertically adjacent lateral sections 112 of the superior and inferior bearing surfaces 101, 102 may be parallel in the coronal plane.

FIG. 5 shows the implant 100 providing 12° of lordotic angulation whereas FIG. 6 shows the implant 100 providing 6° of lordotic angulation. In use, a surgeon may select an implant 100 having lordotic angulation according to a desirous spinal curvature.

In embodiments, the lateral sections 112 of either the superior bearing surface 101 or the inferior bearing surface 102 are not colinear in the coronal plane about the sagittal plane for the correction of scoliosis. For example, vertically adjacent lateral sections 112 may widen apart distally.

The foregoing description, for purposes of explanation, used specific nomenclature to provide a thorough understanding of the invention. However, it will be apparent to one skilled in the art that specific details are not required in order to practise the invention. Thus, the foregoing descriptions of specific embodiments of the invention are presented for purposes of illustration and description. They are not intended to be exhaustive or to limit the invention to the precise forms disclosed as obviously many modifications and variations are possible in view of the above teachings. The embodiments were chosen and described in order to best explain the principles of the invention and its practical applications, thereby enabling others skilled in the art to best utilize the invention and various embodiments with various modifications as are suited to the particular use contemplated. It is intended that the following claims and their equivalents define the scope of the invention.

The term "approximately" or similar as used herein should be construed as being within 10% of the value stated unless otherwise indicated.

The invention claimed is:

1. An intervertebral fusion cage implant, comprising:
the intervertebral fusion case implant being elongate; and defining superior and inferior bearing surfaces,
the inferior bearing surface having vertebral body engaging interferences; and
the superior bearing surface having:
a smooth surface profile;
sagittal plane convexity, the sagittal plane convexity defining a sagittal plane axis rising anteriorly with respect to a horizontal sagittal plane axis; and
sagittal plane curvature asymmetry, wherein:
the superior bearing surface defines a central section having coronal plane convexity and
lateral sections adjacent the central section and wherein the implant is sized so that the central section bears against a central endplate of an adjacent vertebra in use and the lateral sections bear against opposite sides of an epiphyseal rim of the adjacent vertebra in use.

2. The implant as claimed in claim 1, wherein the interferences comprise longitudinal serrations.

3. The implant as claimed in claim 2, wherein the serrations run mediolaterally.

4. The implant as claimed in claim 2, wherein each serration defines an anterior edge which is at a greater angle with respect to a transverse plane of the implant as compared to a posterior edge thereof.

5. The implant as claimed in claim 1, wherein the implant is wider in a sagittal plane of the implant towards an anterior surface of the implant as compared to towards a posterior surface of the implant.

6. The implant as claimed in claim 1, wherein surfaces of the lateral sections extend parallel with respect to a transverse plane of the implant.

7. The implant as claimed in claim 1, wherein surfaces of the lateral sections rise laterally with respect to a transverse plane of the implant.

8. The implant as claimed in claim 1, wherein the inferior bearing surface defines a central section having coronal plane convexity and inferior lateral sections adjacent the central section.

9. The implant as claimed in claim 8, wherein surfaces of the inferior lateral sections extend parallel with respect to a transverse plane of the implant.

10. The implant as claimed in claim 8, wherein surfaces of the inferior lateral sections rise laterally with respect to a transverse plane of the implant.

11. The implant as claimed in claim 1, wherein the superior and inferior bearing surfaces are parallel in a coronal plane of the implant at the lateral sections of the superior bearing surface and at lateral sections of the inferior bearing surface, respectively.

12. The implant as claimed in claim 1, further comprising at least one osseointegration cavity open between the superior and inferior bearing surfaces.

13. The implant as claimed in claim 12, wherein the implant comprises a pair of laterally spaced osseointegration cavities.

14. The implant as claimed in claim 13, wherein the superior bearing surface has sagittal plane continuity between the laterally spaced osseointegration cavities.

15. The implant as claimed in claim 13, wherein the osseointegration cavities are rectangular in a transverse plane of the implant.

16. The implant as claimed in claim 1, wherein the implant defines anterior and posterior surfaces and wherein the anterior and posterior surfaces are planar.

17. The implant as claimed in claim 1, further comprising at least one threaded placement instrument socket through a lateral side of the implant.

18. The implant as claimed in claim 17, wherein a first threaded placement instrument socket extends laterally along a lateral plane of the implant and a second placement instrument socket extends more anteriorly than the first threaded placement instrument socket.

19. The implant as claimed in claim 1, wherein surfaces of the lateral sections of the superior bearing surface are not colinear in a coronal plane of the implant.

20. The implant as claimed in claim 19, wherein the surfaces of the lateral sections of the superior bearing surface rise in a lateral plane of the implant.

* * * * *